United States Patent [19]
Chen et al.

[11] Patent Number: 5,782,896
[45] Date of Patent: Jul. 21, 1998

[54] USE OF A SHAPE MEMORY ALLOY TO MODIFY THE DISPOSITION OF A DEVICE WITHIN AN IMPLANTABLE MEDICAL PROBE

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 788,448

[22] Filed: Jan. 29, 1997

[51] Int. Cl.$^6$ .................................. A61N 5/06; A61N 5/00
[52] U.S. Cl. .................................. 607/88; 607/92; 607/89; 604/95; 606/14
[58] Field of Search .................................. 607/88, 92, 120, 607/122, 126–128, 692; 606/7, 8, 10, 13–16, 17, 19, 78; 74/22 R, 22 A; 604/95, 88, 115, 119, 120, 132, 280–283; 600/179

[56] References Cited

U.S. PATENT DOCUMENTS

| | | |
|---|---|---|
| 4,439,197 | 3/1984 | Honda et al. . |
| 4,507,115 | 3/1985 | Kambara et al. . |
| 4,774,923 | 10/1988 | Hayashi . |
| 4,953,564 | 9/1990 | Berthelsen ............ 128/784 |
| 4,984,581 | 1/1991 | Stice . |
| 5,025,799 | 6/1991 | Wilson . |
| 5,045,064 | 9/1991 | Idriss . |
| 5,090,956 | 2/1992 | McCoy . |
| 5,143,085 | 9/1992 | Wilson ............ 128/772 |
| 5,211,183 | 5/1993 | Wilson . |
| 5,243,996 | 9/1993 | Hall . |
| 5,349,964 | 9/1994 | Imran et al. . |
| 5,370,608 | 12/1994 | Sahota ............ 604/20 |
| 5,383,923 | 1/1995 | Webster, Jr. . |
| 5,409,483 | 4/1995 | Campbell ............ 606/15 |
| 5,445,608 | 8/1995 | Chen ............ 604/20 |
| 5,447,533 | 9/1995 | Vachon et al. . |
| 5,531,685 | 7/1996 | Hemmer et al. . |
| 5,531,780 | 7/1996 | Vachon ............ 607/120 |

OTHER PUBLICATIONS

Lee, DJ, et al., "Development of a New Blood Pump Using a Shape Memory Alloy Actuator," From the Department of biomedical Engineering, Seoul National University, Seoul National University Hospital, pp. M765–M768.

*Primary Examiner*—Jennifer Bahr
*Assistant Examiner*—Roy D. Gibson
*Attorney, Agent, or Firm*—Ronald M. Anderson

[57] ABSTRACT

An implantable probe having an elongated sheath with provision for remotely positioning a device disposed within the elongated sheath. In one embodiment, the device is a circuit board, and a shape memory alloy (SMA) such as Nitinol is used to fabricate one or more actuators that are coupled to the circuit board. The shape memory effect exhibited by the SMA actuator is thermally activated. Electrical current is selectively applied to the actuator to resistively heat the SMA to a temperature sufficient to change its shape. When the shape of the SMA changes, the actuator moves the circuit board or other device longitudinally within the elongated sheath so that the light emitted is directed to a different portion of a treatment site. In another embodiment, the circuit board is rotated about its longitudinal axis within the sheath. In still another embodiment, the actuator moves a piston so as to pump a fluid through a pair of lumens disposed within the sheath to dissipate heat produced by the light emitting devices in a remotely disposed heat exchanger. Another embodiment uses the actuators to both circulate the fluid and move a circuit board.

28 Claims, 7 Drawing Sheets

USE OF A SHAPE MEMORY ALLOY TO MODIFY THE DISPOSITION OF A DEVICE WITHIN AN IMPLANTABLE MEDICAL PROBE

FIELD OF THE INVENTION

The present invention generally relates to apparatus and a procedure for changing the position of a medical device that is implanted within a patient's body, and more specifically, to the use of a shape memory metal alloy for changing the position of a medical device.

BACKGROUND OF THE INVENTION

Several different embodiments of light emitting probes for administering photodynamic therapy (PDT) to an internal site within a patient's body are disclosed in commonly assigned U.S. Pat. No. 5,445,608. Further, a number of embodiments of flexible light emitting probes are disclosed in commonly assigned pending U.S. patent application, Ser. No. 08/613,390, and a continuation-in-part patent application thereof, Ser. No. 08/633,171, both entitled, "Flexible Microcircuits for Internal Light Therapy." In the above-referenced patent, it is generally contemplated that a probe containing a plurality of light sources can be transcutaneously introduced to a desired treatment site through a surgical incision and then left in place for an extended period of time so that the light emitted by light emitting diodes (LEDs) or other types of light sources included in the probe can administer PDT to destroy abnormal tissue or other types of pathogenic organisms that have absorbed a photodynamic agent. Similarly, the flexible microcircuits of the above-noted pending patent applications are generally intended to be introduced into the body through a natural opening or through a small incision and positioned at the treatment site using conventional endoscopic techniques. These prior invention disclosures teach that a flexible probe may be fixed at a treatment site using sutures, staples, or a biocompatible adhesive. While any of the techniques that are used for attaching a medical device to a site within a patient's body can effectively anchor a light emitting probe in a desired position, additional time and steps are required for a surgeon to endoscopically relocate or reposition a device after it has been implanted at a treatment site, so that it can treat a different portion of the site. For example, a tumor to which PDT is being administered by an implanted probe may be relatively large compared to an area irradiated by light emitted by the light source in the probe. After a part of the tumor is treated and the abnormal cells comprising that part have been destroyed, it may be necessary for a surgeon to rotate or otherwise reposition the implanted probe so that the remaining area can be subjected to PDT.

Each time that an endoscopic technique is applied to manipulate the probe and change its position to treat a different area, the patient will be exposed to additional risk and discomfort. Clearly, in such cases, it would be preferable to remotely reposition the probe to administer PDT to a different portion of the tumor or treatment site. The fixed or flexible implantable probes disclosed in the above-cited commonly owned references do not provide any mechanism for remotely repositioning the light source within the probes. Furthermore, the repositioning of the light source in a probe should preferably be accomplished by supplying an appropriate electrical signal to the probe to cause the repositioning behavior. Depending on the size and topography of the treatment site, it may be necessary to reposition the light source (or other medical device in the probe that provides the desired medical therapy) by a longitudinal displacement or by a rotational displacement. Accordingly, it would be desirable to provide probes in which at least one of these two types of displacement or repositioning of a light source or other medical device is accomplished in response to a remotely provided electrical signal.

One approach for remotely manipulating a device employs a shape memory alloy (SMA). SMAs are a family of alloys having anthropomorphic qualities of memory and trainability. These alloys possess attributes that make them especially useful for manipulating a medical device. A particularly useful attribute of an SMA is that when it is plastically deformed at a particular temperature, it can completely recover its original shape on being raised to a higher predefined temperature. In recovering its original shape, the SMA produces a powerful displacement force that can be 200 times greater than a force produced by the expansion and contraction of a bimetallic element of the same weight. Moreover, a particular SMA can be selected so that the return to the memory shape occurs at a predetermined desired temperature. To produce an SMA element that has a desired single memory shape, the SMA is formed into the desired shape and heated to a temperature so that the crystalline temperature of the SMA is entirely in a beta or austenite phase. The SMA element is then cooled below a defined and characteristic temperature $M_f$ at which the austenite crystal structure of the alloy changes to a martensite crystal structure. The SMA element can then be plastically deformed into a different shape. If the SMA element is then heated above another defined temperature $A_r$ (where $A_r > M_f$) at which the martensite crystalline structure of the alloy is again converted to the austenite crystalline structure, the SMA moves and exerts force as it reverts back into its memory shape. This process can be repeated indefinitely.

In 1962, an SMA of nickel and titanium (referred to as "Nitinol") was discovered. Nitinol alloy is an SMA that can retain memory shapes for two different physical configurations of the alloy, at two different temperatures through a process of trainability. Trainability of the Nitinol alloy is based upon the fact that the alloy exhibits superelasticity, i.e., the growth and compensating contraction of adjacent plates of the martensite crystalline structure as stress is applied. The training of a Nitinol alloy (and other SMAs) for two different shape memory configurations is generally accomplished by limiting the number of variants of martensite formed when an alloy is repeatedly heated and cooled below the critical temperature $M_f$.

U.S. Pat. No. 5,531,780 (Vachon) discloses a lead having an advancable electrode that is selectively deployable for use with an implantable cardiac pacemaker. The lead is inserted at a desired location within the patient's body, and a distal tip of the electrode is extended and retracted from the tubular body of the lead by an SMA actuator. Further, the electrode may serve to center or anchor the lead in a desired position at the patient's heart. The reference also teaches that the distal tip can serve as an anti-inflammatory drug delivery system to reduce the buildup of fibrous tissue around the cardiac pacemaker. Consequently, Vachon solves the problem of remotely positioning an electrode for the delivery of drugs and electrical shocks to a patient's heart. It will be appreciated that an entirely different solution is required to enable a user to remotely position a device such as a light source within an elongated sheath or probe disposed inside a patient's body.

Another problem sometimes associated with probes used to administer PDT is the need to dissipate heat produced by the light source in the probe. Although mild heating of the tissue at a treatment site can actually improve the efficacy of PDT, for some types of treatment sites and if light emitting devices are used that emit substantial heat, the temperature of the probe may rise to levels that can damage the normal tissue surrounding the probe. In this case, it will clearly be desirable to convey the excess heat of the probe away from the treatment site and dissipate it over a larger area so that the temperature at the treatment site does not rise to an unacceptable level. One technique for cooling a probe is to circulate a fluid through the probe and to a remote heat exchanger that harmlessly dissipates the heat to tissue surrounding the heat exchanger. However, a complex pump for circulating fluid is impractical for use in a probe. Instead, a simple piston or diaphragm pumping mechanism is needed to circulate a fluid through the probe. Again, an SMA can be used to provide the driving force to circulate a fluid. None of the prior art discloses the use of an SMA drive element for pumping fluid through a medical probe to cool it. In some instances, it may be desirable to employ the same SMA drive element used to move the light source for dual purposes, i.e., so that PDT can be administered to an extended area, and so that a piston or a diaphragm can be actuated to circulate fluid through the probe to provide cooling.

SUMMARY OF THE INVENTION

In accordance with the present invention, apparatus is defined that includes an enclosed probe in which a position of a device within the probe is selectively changed. The apparatus includes an actuator comprising a shape memory metal. The shape memory metal has a first shape associated with a first state and a second shape associated with a second state, and changes from the first state to the second state as a function of temperature. Also included is a device that is movably coupled to the actuator. An elongated sheath contains the device and the actuator and has a proximal end and a distal end. Means are provided for changing the temperature of the actuator, causing it to transition from the first state to the second state and thereby move the device within the sheath.

In one embodiment, the first shape of the actuator is a coiled helix; in its second shape, the actuator is substantially straighter and substantially longer, so that when the actuator transitions between the first and second shapes, it provides a linearly directed driving force. In an alternative embodiment, the actuator rotates through a substantial angle when transitioning between the first shape and the second shape, thereby rotating the device within the sheath. In still another embodiment, the first shape of the actuator is serpentine, and the second shape of the actuator is substantially straight, so that the actuator moves the device along a longitudinal axis of the probe that extends between the distal and proximal ends of the sheath as the actuator transitions between the first shape and the second shape. If necessary to increase the driving force applied to the device, a plurality of shape memory elements may be employed.

In still another embodiment, the actuator is elongate and has two opposite ends. In this embodiment, the actuator twists when transitioning between the first shape and the second shape, causing the device to rotate about an axis.

In one preferred form of the invention, the device comprises a light source. This light source preferably comprises a plurality of light emitting devices. Further, the light source may comprise either an LED, a laser source, an incandescent source, a fluorescent source, or an electroluminescent source.

In one embodiment, the means for changing the temperature comprise a resistive heating element that produces heat when the resistive heating element is energized with an electrical current. More broadly, the means for changing the temperature comprise either a thermal source that is hotter than the actuator and conveys thermal energy to the actuator to heat it, or a thermal sink that is colder than the actuator and conducts thermal energy away from the actuator to cool it.

Another embodiment of the present invention is directed to cooling the probe. In this embodiment, the device comprises a first lumen and a second lumen that extend along a longitudinal axis of the sheath, and a pump. A heat exchanger located remotely away from the probe has an inlet coupled in fluid communication with the first lumen, and an outlet coupled in fluid communication with the second lumen. The first lumen, second lumen, and heat exchanger comprise a closed fluid path in which the pump is disposed. The pump includes a check valve that permits fluid to flow in a first direction within the closed fluid path, but prevents fluid flow in a second direction, which is generally opposite the first direction. A heat transfer fluid is disposed within the closed fluid path. The heat transfer fluid conveys heat away from the probe and dissipates the heat in the heat exchanger when circulated along the closed fluid path. Displacement of the heat transfer fluid occurs as the actuator transitions between the first and second shapes. The actuator is preferably coupled to drive a piston that is reciprocatively displaced in the first and second directions by the actuator as the actuator transitions between its first and second shapes. Nitinol alloy is preferably used for the shape memory metal.

In one form of the invention, the device further comprises a light source that generates the heat that is conveyed away from the probe by the heat transfer fluid. The light source is preferably mounted on a divider disposed between the first and second lumens. The piston is also preferably disposed within one of the first and second lumens and includes a seal around its periphery. The seal generally prevents the heat transfer fluid from flowing past the periphery of the piston—at least when the piston is moving in the first direction.

In one preferred form of the invention, the check valve comprises a captive ball that seals an orifice through the piston when the piston is moving in the first direction, but moves away from the orifice to permit the heat transfer fluid to flow through the orifice when the piston is moving in the second direction. In another preferred embodiment, the check valve comprises the seal. In this case, the seal includes an elastomeric flange around its periphery that moves radially inward toward a center of the piston and enables the heat transfer fluid to flow past the flange as the piston is displaced in the second direction, but is forced radially outward by a pressure developed in the heat transfer fluid and prevents fluid flow past the piston as the piston is displaced in the first direction.

While other alternatives for dissipating the heat can be used, one embodiment of the heat exchanger comprises a section of catheter that is coupled to the probe. This section of catheter also includes a first lumen and a second lumen that are respectively coupled to the first and second lumens in the probe and are coupled together by a crossover port disposed at a point spaced apart from the probe.

Another aspect of the present invention is directed to a method for changing a position of a device within a probe that is disposed within a patient's body. The method includes steps that are generally consistent with the functions provided by the elements of the apparatus described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The present invention uses a shape memory alloy (SMA) to remotely and selectively displace the position of a device within an elongated sheath of a probe that is disposed within a patient's body. As discussed in detail below, FIGS. 1 through 17 illustrate various embodiments and aspects of the present invention. In each embodiment, one or more SMA actuators are remotely activated by a medical practitioner to move a device, such as a light emitting circuit or piston, within the elongated sheath. Further, the remotely controlled positioning of the device enables PDT (or other medical therapy) to be administered to a treatment site surrounding the probe, over a larger area than would be possible without the remotely actuated repositioning of the device provided by the present invention.

The present invention uses one or more actuators formed of Nitinol SMA. As noted above, Nitinol is an SMA that can retain shape memories for two different physical configurations of the alloy, to which the material changes as a function of temperature. The training of a Nitinol alloy (and other SMAs) to a memory shape is generally accomplished by a five step sequence, as follows: (1) the alloy's temperature is raised to a first characteristic temperature and the alloy is plastically deformed into a first shape; (2) the shaped alloy is heated above the first temperature until austenite crystals form within the alloy's molecular structure; (3) the twice heated alloy is quenched or quickly cooled to a lower temperature at which the austenite crystals break apart and martensite crystals start to form in the alloy's molecular structure; (4) the cooled alloy having a substantially martensite molecular structure is plastically deformed into a second shape at this lower temperature; and, (5) the previous four steps are repeated until the first and second shapes spontaneously occur in the alloy, respectively, when austenite and martensite crystals form in the molecular structure of the alloy as a function of temperature.

The temperature at which a shape is "memorized" by an SMA is a function of the temperatures at which martensite and austenite crystals form in that particular alloy. Further, crystal formation temperatures are a function of the metallic composition of the particular alloy used and any stresses applied during the crystal formation process. The Nitinol family of alloys can be fabricated so that the shape memory effect will occur at any point over a range of −270° to +100° Celsius. However, it is contemplated that the present invention can alternatively be fabricated using SMAs that are substantially different in composition than Nitinol. Recently, a new family of SMAs based on copper, zinc, and aluminum has been developed. These SMAs have a range of crystal formation temperatures that are similar to Nitinol, and shape memory training of the new alloys is performed in substantially the same manner as discussed above.

The selection of a particular SMA for an actuator to position a device within the sheath of a probe requires the careful consideration of several parameters: (1) metallic composition of the alloy; (2) the austenite and martensite crystal formation temperatures; (3) the stresses that may be applied during crystal formation; and (4) the amount of force and deflection required of the actuator.

Figure 1:
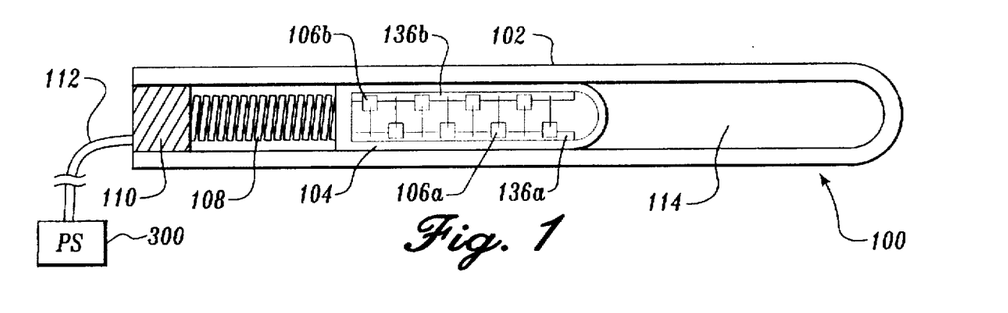
FIG. 1 is a side sectional view of a probe with a movable device coupled to an SMA actuator that has a helix shape.
Figure 2:
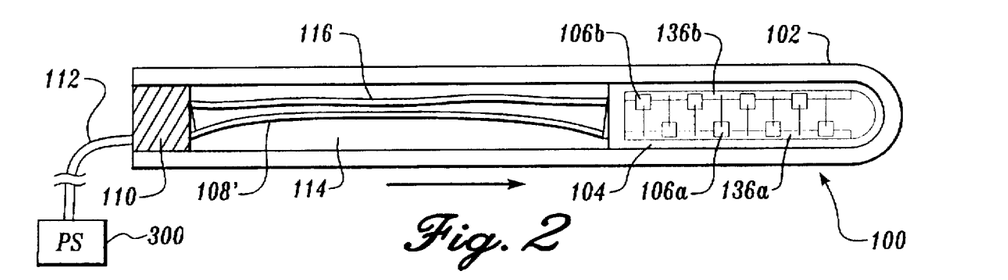
FIG. 2 is a side sectional view of the probe of FIG. 1, illustrating the actuator in an extended position after the SMA has undergone a change in state.

A first embodiment of the present invention is illustrated in FIGS. 1 and 2. In FIG. 1, a probe 100 is shown that includes an elongated, optically transparent sheath 102, which contains a circuit board 104, a base 110, a lead 112, and an actuator 108. In FIG. 1, actuator 108 is illustrated in a retracted position in which the actuator has a helical shape. Light emitting devices 106a and 106b are mounted, respectively, to a pair of conductive traces 136a and 136b, along opposite edges of circuit board 104, and are arranged in a spaced-apart array along the length of the circuit board. A power supply 300 is coupled through a lead 112 to actuator 108 and conductive traces 136a and 136b. The conductive traces are energized by an electrical current from power supply 300, so that PDT can be administered to a treatment site surrounding sheath 102, within the patient's body. Only one surface of the circuit board 104 is visible in the Figures, but the other side is identical, including additional light emitting devices mounted thereon. Actuator 108 is used to move circuit board 104 between a first position (shown in FIG. 1) and a second position (shown in FIG. 2) within an internal volume or cavity 114 of sheath 102. Referring to FIG. 2, circuit board 104 is shown in its second position to which it is moved when the actuator experiences a shape change. It will be apparent that the memory shape of actuator 108' is much straighter than the helical shape of actuator 108. Furthermore, when the actuator changes shape, it elongates, moving circuit board 104 longitudinally within sheath 102, so that the light emitted by light emitting devices 106a and 106b is administered to a different portion of the surrounding treatment site. A lead 116 extends between base 110 and circuit board 104. Lead 116 coils inside the helical-shaped actuator 108 and then stretches along the longitudinal axis of the probe as the SMA changes to the shape of actuator 108'.

A medical practitioner using the first embodiment of the present invention employs the following method to selectively move circuit board 104 along the longitudinal axis of probe 100, after the probe has been positioned at a treatment site inside a patient's body. First, an electrical current from power supply 300 is provided by lead 112 through base 110 to actuator 108 in the retracted position. The return flow of electrical current to the power supply is through lead 116 (and through lead 112). The flow of electrical current through actuator 108 causes a resistive heating to occur that substantially increases its temperature. As actuator 108 heats above its austenite phase change temperature, austenite crystals form in the molecular structure of the SMA comprising actuator 108. Once austenite crystals start to form, the shape memory effect cause the SMA to rapidly change from the helical shape of actuator 108 into the substantially straight shape of actuator 108', and move circuit board 104 from the first position to the second position within cavity 114 of elongated sheath 102. The extended position of the actuator is maintained until the flow of electrical current from power supply 300 is halted. Additionally, light emitting devices 106a and 106b, which are mounted on circuit board 104, receive electrical current from power supply 300 via leads 112 and 116, so that when energized, they irradiate the tissues at the treatment site surrounding sheath 102.

After the user interrupts the flow of electrical current through the actuator, actuator 108' begins to cool, reaching a lower temperature at which the austenite crystals convert to martensite crystals. At the onset of martensite crystal formation, the shape memory effect causes actuator 108' to rapidly revert from its substantially straight shape into the helical shape of actuator 108. Further, the shape change causes the actuator to quickly retract circuit board 104 from the distal end of cavity 114 back towards the proximal end. After the actuator has returned to the retracted position, power supply 300 continues to supply electrical current to light emitting devices 106a and 106b, so that tissue in the portion of the treatment site surrounding the proximal end of cavity 114 is irradiated with light.

Figure 3:
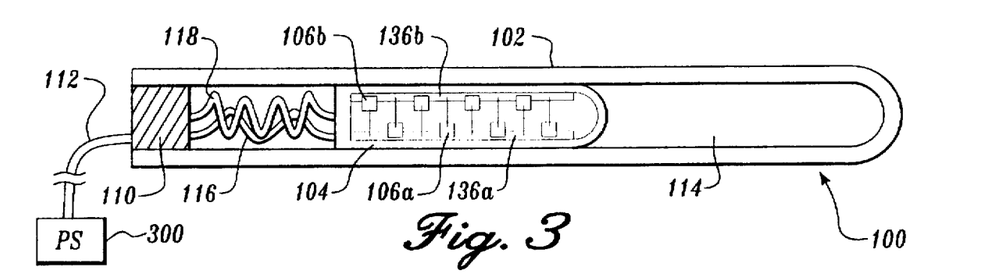
FIG. 3 is a side sectional view of a second embodiment of the present invention, illustrating an SMA actuator in a serpentine shape.
Figure 4:
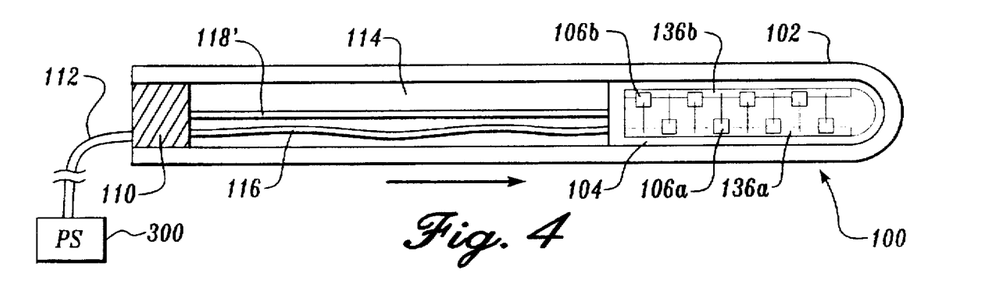
FIG. 4 is a side sectional view of the probe of FIG. 3, showing the SMA actuator in an extended position after it has experienced a shape change.

A second embodiment of the present invention is displayed in FIGS. 3 and 4 and is substantially similar to the first embodiment discussed above. An important difference between the two embodiments is that the second embodiment uses an actuator 118 having a serpentine shape in the retracted position, instead of a helical shape. In FIG. 3, probe 100 has circuit board 104 disposed at the proximal end of cavity 114, with actuator 118 in the retracted position in which it has a serpentine shape. Also, power supply 300 is shown coupled by leads 112 and 116 to actuator 118 and light emitting devices 106a and 106b.

Turning now to FIG. 4, circuit board 104 has been moved toward the distal end of cavity 114 by actuator 118', which has a substantially straight shape. In a manner substantially similar to the first embodiment, light emitting devices 106a and 106b receive electrical current from power supply 300 through leads 112 and 116 so as to irradiate the tissues surrounding sheath 102 in each position of the circuit board.

A user of the second embodiment employs actuator 118 in substantially the same manner as discussed above for the first embodiment. The method for extending and retracting the circuit board within the sheath as disclosed above for the first embodiment is generally applicable to the second embodiment of the present invention.

Figures 5, 6, 7:
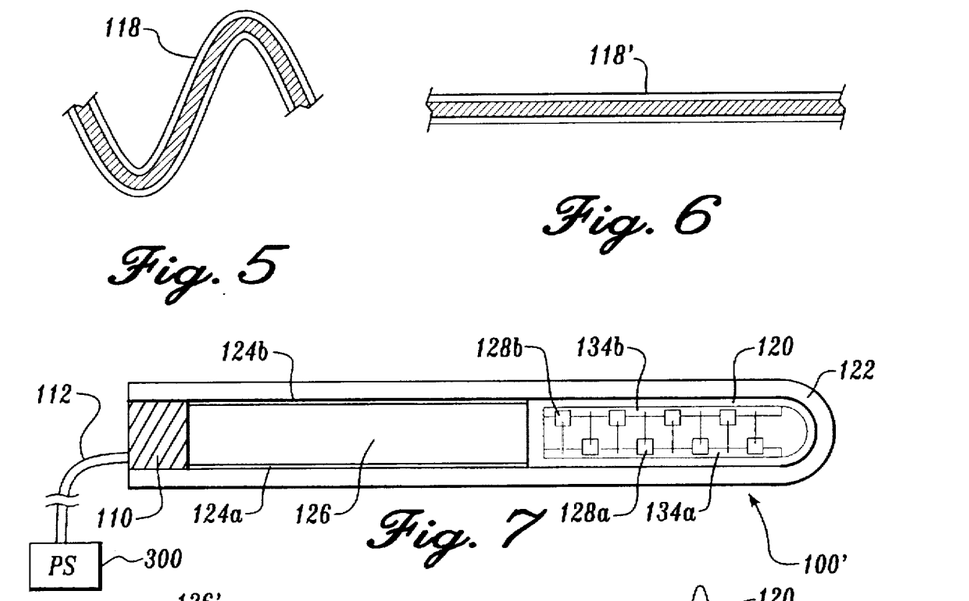
FIG. 5 is a side sectional view of a portion of the SMA actuator having a serpentine shape.
FIG. 6 is a side sectional view of a portion of the SMA actuator shown extended into a substantially straight shape.
FIG. 7 is a side sectional view of a third embodiment of the present invention, showing a probe with an SMA actuator that is flat.

Referring now to FIG. 5, a portion of actuator 118 has a serpentine shape when the actuator is retracted. The serpentine shape is achieved when the crystal structure of the SMA comprising the actuator is in the martensite phase. In FIG. 6, a portion of actuator 118' is shown in its extended straight shape. The substantially straight shape of actuator 118' results from the formation of austenite crystals in the molecular structure of the SMA comprising the actuator, as explained above.

Figure 8:
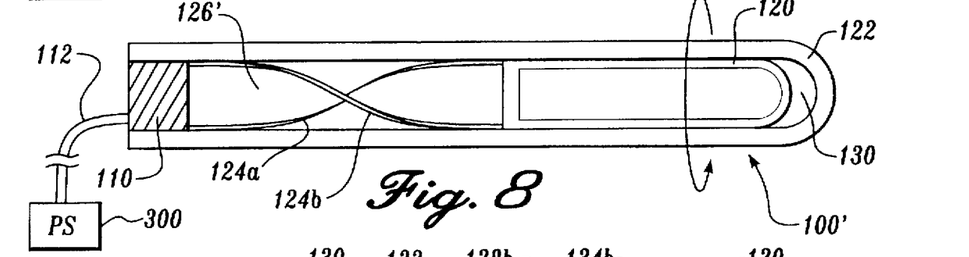
FIG. 8 is a side sectional view of the probe of FIG. 7, illustrating the rotational twist of the SMA actuator after it is heated sufficiently to change shape.

A third embodiment of the present invention is shown in FIGS. 7 and 8. In the third embodiment, the present invention provides for rotating a circuit board 120 within the distal end of an elongated sheath 122 to provide PDT to surrounding tissues by light emitted from a probe 100'. In FIG. 7, light emitting devices 128a and 128b are mounted, respectively, on a pair of conductive traces 134a and 134b, along the edges of circuit board 120, in a spaced-apart array. No light emitting devices are disposed on the opposite surface of the circuit board. A pair of leads 124a and 124b extend along the opposite edges of a vane actuator 126, between base 110 and circuit board 120. Further, vane actuator 126 has a substantially planar shape and is aligned with circuit board 120 in sheath 122.

Referring to FIG. 8, the actuator is displayed after it has experienced a change to its memory configuration, i.e., as actuator 126', which is twisted through an angle of about 180° relative to the planar shape of actuator 126. As a result of a foreshortening effect that results from the rotation and twisting of the actuator, circuit board 120 is retracted slightly away from distal end of sheath 122. More importantly, the change in the shape of the actuator rotates circuit board 120 through an angle of about 180°. Also, light emitting devices 128a and 128b shown in FIG. 7 are now positioned so that the light they emit is directed toward an opposite side of the treatment site. Additionally, power supply 300 is coupled by leads 112, 124a, and 124b to light emitting devices 128a and 128b, so that an electrical current from the power supply 300 energizes the light emitting devices.

A medical practitioner using the third embodiment of the present invention positions probe 100' at the treatment site inside the patient's body and supplies an electrical current from power supply 300 to the light emitting devices, which administer PDT to the treatment site on one side of the probe 100'. When the light therapy is completed on the first side of the probe, the medical practitioner selectively enables an electrical current supplied by the power supply via lead 112 to flow through actuator 126. The flow of electrical current through actuator 126 causes a resistive heating that substantially increases the temperature of the actuator. As the temperatures increase above the austenite phase change temperature of the SMA comprising actuator 126, austenite crystals form in the molecular structure of the SMA. Once austenite crystals start to form, the shape memory effect causes actuator 126 to rapidly change from its substantially planar shape into the twisted helical shape of actuator 126', rotating circuit board 120 within a cavity 130 of sheath 122. Further, light emitting devices 128a and 128b, which are mounted on circuit board 120, are thus repositioned to direct light toward the treatment site on the opposite side of the probe.

After the user interrupts the flow of electrical current from power supply 300 to actuator 126', it begins to cool to a temperature at which the austenite crystals break apart and reform as martensite crystals. At the onset of martensite crystal formation, the shape memory effect causes actuator 126' to rapidly revert to the planar shape of actuator 126. It may be useful in some cases to alternately irradiate opposite sides of the treatment site by repetitively causing the configuration of the SMA to change between the shapes of actuator 126 and 126', so that the circuit board is rotated back and forth between the positions in which it is shown in FIGS. 7 and 8. For example, it may be helpful to administer PDT to one side of the treatment site for only a limited time period to prevent overheating of normal tissue surrounding the treatment site. By repetitively rotating the circuit board, the heating of the treatment site on each side can be minimized during the treatment. It is also contemplated that actuator 126' may rotate the circuit board through other angles. For instance, if light emitting devices are provided on both surfaces of the circuit board, it would be desirable to rotate the circuit board through an angle of about 90° to ensure the light emitted from opposite sides of the circuit board is directed toward each of the four quadrants of the treatment site surrounding probe 100'.

Figure 9:
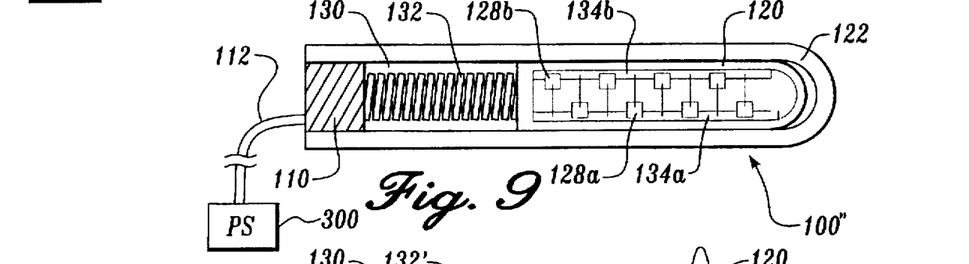
FIG. 9 is a side sectional view of a fourth embodiment of a probe in which a helical coil-shaped SMA actuator is coupled to a device, showing the disposition of the device while the SMA is in one state.
Figure 10:
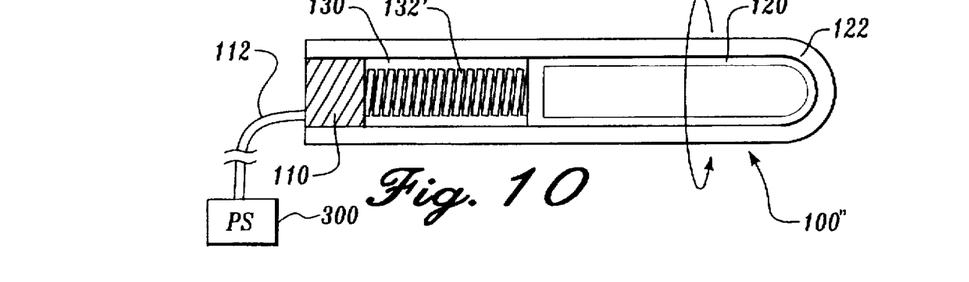
FIG. 10 is a side sectional view of the probe shown in FIG. 9, after the SMA actuator has changed shape, showing the device coupled to the actuator after the device is rotated.

A fourth embodiment of a probe 100'' is displayed in FIGS. 9 and 10; probe 100'' is substantially similar to the third embodiment discussed above. The primary difference between the third and fourth embodiments is that the latter embodiment employs an actuator 132 that has a helical coil shape and when heated, changes by rotating and slightly lengthening, causing circuit board 120 to rotate and move slightly along the longitudinal axis.

In FIG. 9, circuit board 120 is illustrated slightly retracted from distal end of cavity 130, with light emitting devices 128a and 128b mounted to couple to conductive traces 134a and 134b along opposite sides of the circuit board. Further, the light emitting devices are mounted on only one surface of circuit board 120. In FIG. 10, actuator 132' is shown after it has changed to a rotated shape memory configuration. This transition causes the helical coil to slightly lengthen and to twist around its central axis so that circuit board 120 is linearly moved into the distal end of cavity 130 in sheath 122 and is rotated about the longitudinal axis of the probe around an angle of about 180°. Light emitting devices 128a and 128b are thus directed toward the opposite side of the treatment site in which probe 100'' is disposed. Additionally, power supply 300 is coupled by lead 112 to actuator 132 and through a lead (not shown) that extends through the center of the helical shaped coil, to conductive traces 134a and 134b. Electrical current from power supply 300 energizes the light emitting devices so that they selectively administer PDT to tissue on opposite sides of the treatment site that surrounds sheath 122. The fourth embodiment is used in the same manner as the third embodiment.

Figure 11A:
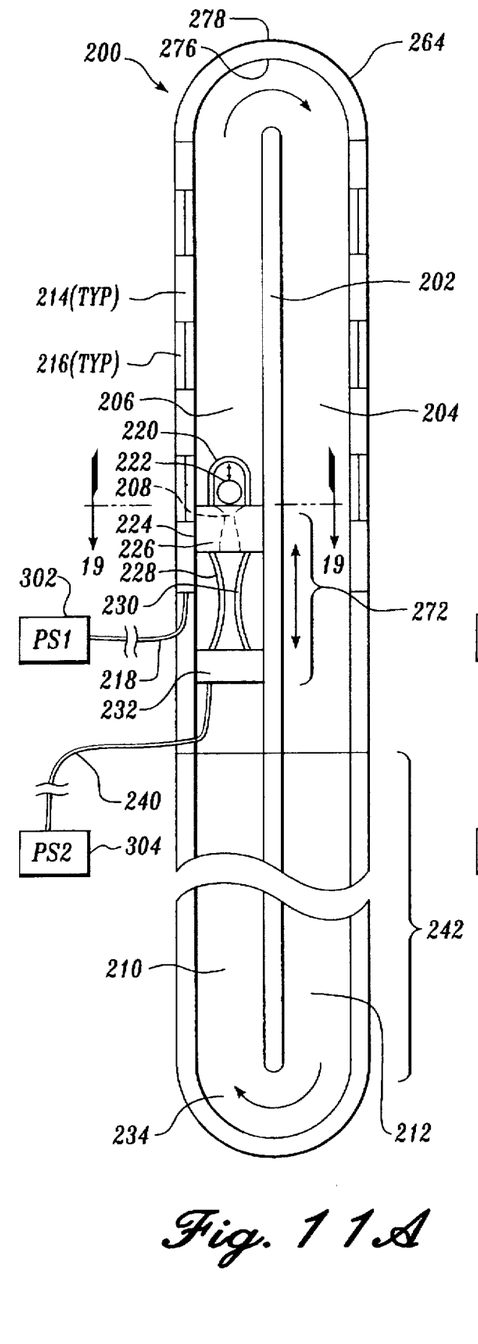
FIG. 11A is a side sectional view of a probe including an elongated sheath having two lumens and a piston assembly coupled to a pair of SMA actuators, illustrating the piston assembly in a first position and the actuators in a retracted position.
Figure 11B:
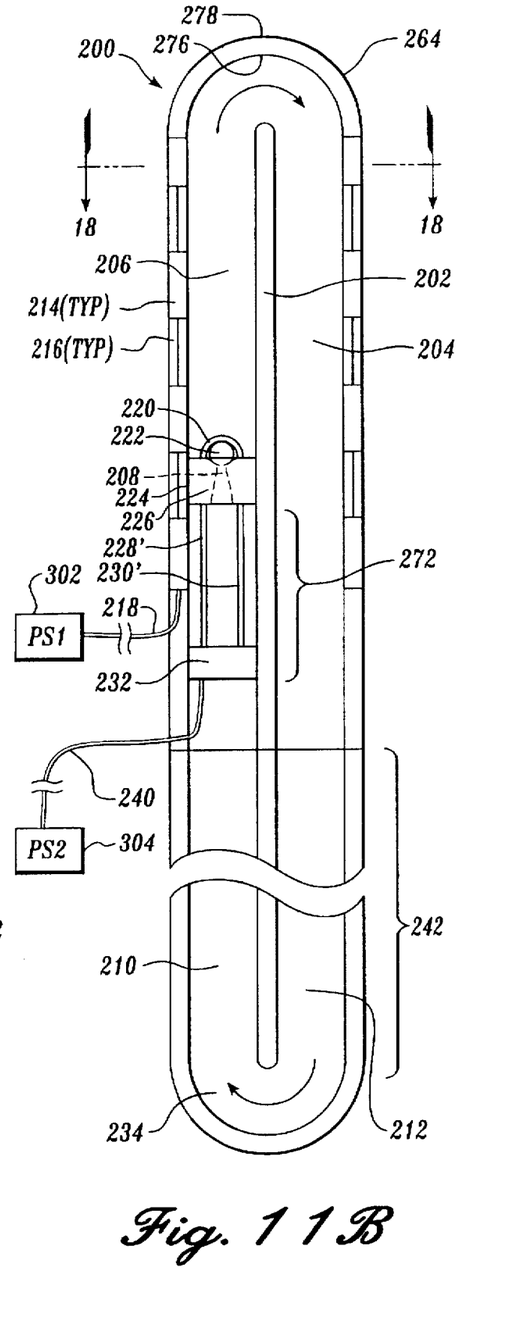
FIG. 11B is a side sectional view of the probe of FIG. 11A, illustrating the piston assembly in a second position with the actuators in an extended position.

A probe 200 that employs the present invention in a different manner is shown in FIGS. 11A and 11B. In FIG. 11A, a plurality of light emitting devices 214, which are electrically coupled in parallel with each other by a plurality of leads 216, are shown disposed between an exterior surface 278 and an interior surface 276 of an elongate sheath 264. Sheath 264 preferably comprises a biocompatible, transparent, plastic polymer. A first power supply 302 is coupled through a lead 218 to leads 216 and provides an electrical current that energizes the light emitting devices to administer PDT. The light emitting devices produce a considerable heat that might cause an unsafe temperature of the tissue surrounding the treatment site at which probe 200 is implanted, if not dissipated.

The interior of probe 200 has a pair of lumens 206 and 204 that are separated by a divider 202, except at the distal end of the interior, where the lumens are in fluid communication with each other. A biologically safe fluid, such as distilled water, generally fills lumens 204 and 206. The lumens are coupled to corresponding lumens 210 and 212 in a catheter 242, only a portion of which is shown. At a proximal end of the catheter, lumens 210 and 212 are connected by a crossover passage 234, forming a closed circuit loop. Catheter 242 comprises a heat exchanger that transfers heat from fluid in the lumens to surround tissue over a relatively larger area so that the surrounding tissue does not experience any significant (or at least, not any harmful) temperature increase due to the heat of the fluid in the lumens of the catheter.

A piston assembly 272, which is disposed in lumen 206, includes a cage 220, a ball 222, a piston 226, an annular base 232, an orifice 208 through the center of the piston, and a pair of actuators 228 and 230 that extend between the base and the piston. A lead 240 connects a second power supply 304 to actuators 228 and 230. In FIG. 11A, actuators 228 and 230 are shown in a retracted position, with ball 222 floating within cage 220, so that fluid behind piston 226 can flow freely through orifice 208. Ball 222 serves as a check valve that seals around the periphery of orifice 208, closing the orifice when the piston moves toward the distal end of sheath 264.

Referring now to FIG. 11B, actuators 228' and 230' have been heated, causing the SMA comprising the actuators to change to the fully extended configuration of the shape memory. As the actuators change from their retracted configuration to their extended configuration, piston 226 is forced toward the distal end of the sheath, causing the ball to seat and close off fluid flow through orifice 208 in the center of piston 226. An outer surface 224 of piston 226 seals against the interior of lumen 206. As shown in FIG. 11B, actuators 228' and 230' are in their extended configuration.

As the actuators move from their retracted configuration as shown in FIG. 11A to their extended configuration shown in FIG. 11B, they move piston 226, forcing fluid to circulate from lumen 206 and lumen 204 in sheath 264 through the catheter. Heat transferred from light emitting devices 214 into the fluid is dissipated through the catheter and into the surrounding tissue. However, because of the length of the catheter, the heat dissipated does not cause any damaging temperature rise in the tissue surrounding the catheter.

After probe 200 is positioned at the treatment site inside the patient's body, an electrical current from first power supply 302 is supplied to light emitting devices 214 by leads 218 and 216. The light emitting devices irradiate the tissue at the treatment site surrounding probe 200. To avoid any deleterious effects caused by the light emitting devices overheating the surrounding tissue, second power supply 304 is selectively repetitively energized, creating a pulsed electrical current that flows through actuators 228 and 230. The current flowing through the actuators resistively heats the SMA comprising the actuators above the temperature at which the alloy transitions from the martensite to the austenite crystalline state. When the rapid change to the memory shape configuration occurs, the actuators extend, closing the check valve and forcing fluid to flow through lumens 206 and 204. Each time that the electrical current flowing through the actuators pulses off, the SMA comprising the actuators cools below the martensite critical temperature point, and the actuators assume their retracted configuration, drawing the piston back within lumen 206. As the piston moves back, the ball floats away from the piston within cage 220, enabling fluid to flow through orifice 208. The repetitive heating and cooling of the actuators thus pumps fluid through the lumens of the sheath and catheter, cooling the light emitting devices and sheath 264 so that normal tissue adjacent the treatment site is not overheated.

Figure 12A:
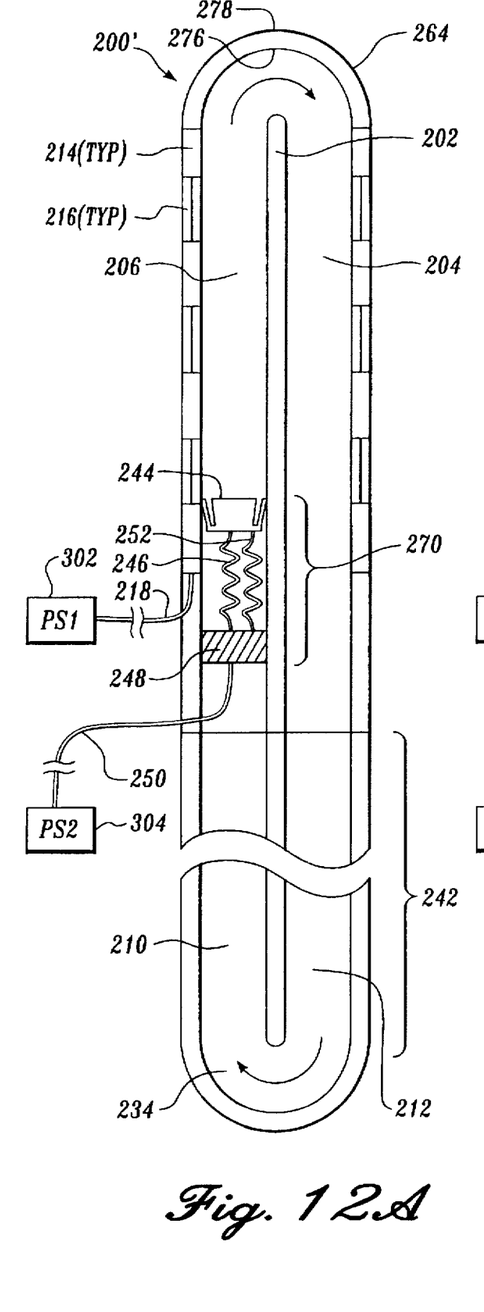
FIG. 12A is a side sectional view of a probe including an elongated sheath having two lumens and a piston coupled to an actuator, illustrating the piston and the actuator in a retracted position.
Figure 12B:
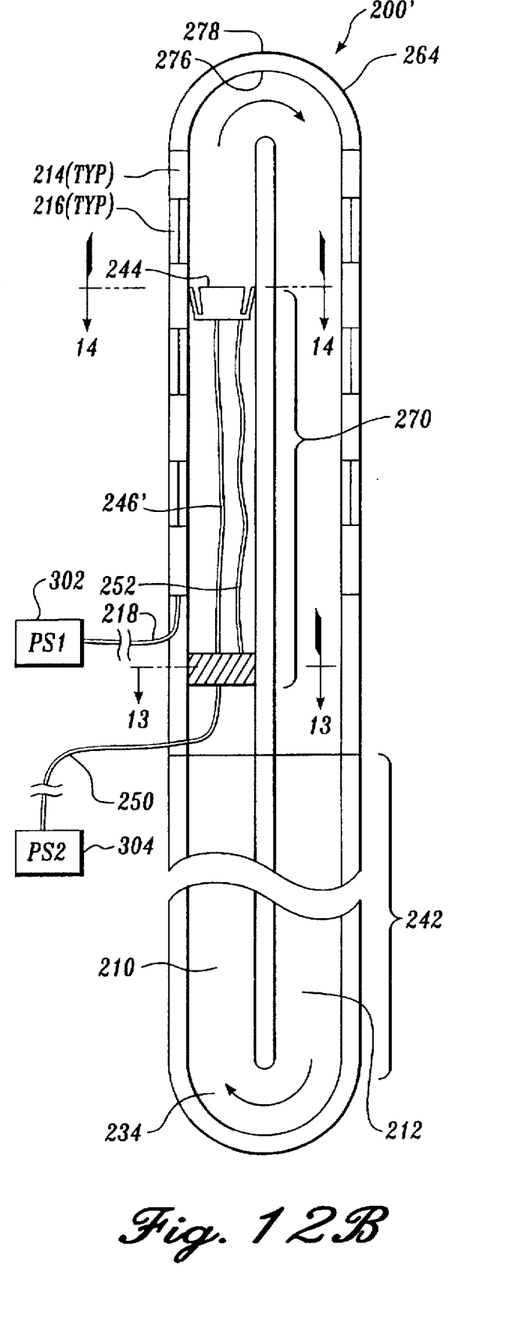
FIG. 12B is a side sectional view of the probe shown in FIG. 12A, displaying the piston and the actuator in an extended position.

A sixth embodiment of the present invention is represented in FIGS. 12A and 12B with two side views of a probe 200'. Although the sixth embodiment is substantially similar to the fifth embodiment, there are important differences between the two. In particular, the sixth embodiment employs a piston assembly 270 to pump fluid that does not include a ball-type check valve. As shown in FIGS. 12A and 12B, probe 200' also includes elongated sheath 264. Further, the piston assembly includes a piston head 244, a base 248, a lead 252, and an actuator 246 having a serpentine shape. The electrical current from second power supply 304 is coupled through a lead 250 to actuator 246 and to lead 252. Similarly, electrical current from first power supply 302 is carried through lead 218 to the plurality of leads 216 that are coupled to light emitting devices 214. In FIG. 12B, piston assembly 270 is shown with actuator 246', which is configured as a substantially straight rod having length substantially greater than that of actuator 246. When the SMA comprising the actuator is cycled between the respective shapes shown in FIGS. 12A and 12B, the piston head is reciprocated back and forth in lumen 206, thereby pumping the fluid through the lumens of the sheath and the catheter to cool the sheath.

Figure 13:
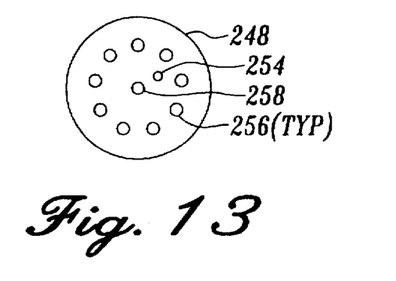
FIG. 13 is a top view of a base of the probe of FIGS. 12A and 12B, showing a plurality of orifices that enable fluid flow through the sheath.
Figure 14:
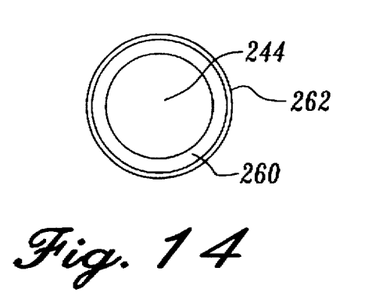
FIG. 14 is a top view of the piston for the probe of FIGS. 12A, 12B, and 13, illustrating an annular U-cup seal that is attached around a periphery of the piston.
Figure 15:
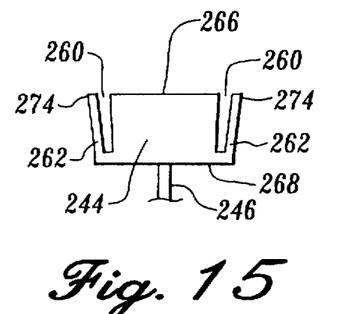
FIG. 15 is a side cross-sectional view of the piston and seal of FIG. 14.

In FIG. 13, the plan view of base 248 illustrates a plurality of orifices 256 through which fluid flow into lumen 206. Further, an orifice 254 is provided for lead 252 and an orifice 258 is provided to receive and couple to the distal end of actuator 246. FIGS. 14 and 15 illustrate a U-shaped seal 262 around the periphery of piston head 244. The seal includes an annular gap 260 that is disposed between the outer circumference of piston head 244 and a lip 274, which extends around the outer edge of the seal. Piston head 244 has a top side 266 and a bottom side 268, which is coupled to actuator 246.

Probe 200' is used in generally the same manner as probe 200. However, there is one significant difference between the two embodiments that should be mentioned. As discussed above, the sixth embodiment only uses one actuator for moving a piston head, whereas, the fifth embodiment uses two actuators to move the piston.

In the sixth embodiment, second power supply 304 provides electrical current to actuator 246 via lead 250, preferably in a pulse form. The flow of electrical current through actuator 246 during the pulse induces a resistive heating that substantially increases its temperature. As the temperature of actuator 246 increases above its austenite phase change temperature, austenite crystals form in the molecular structure of the SMA comprising the actuator. Once the austenite crystals start to form, the shape memory effect causes actuator 246 to rapidly change from a serpentine shape into that of a substantially straight rod shape. As the actuator 246 moves from its retracted position to its extended position (246'), it forces piston head 244 up along the longitudinal axis of lumen 206. The movement of piston head 244 forces U-shaped seal 262 outwardly against the inner wall of lumen 206, so that the width of annular gap 260 is increased, and a fluid seal is formed between the lumen wall and lip 274. Further, piston head 244 displaces the fluid above top side 266, so that the fluid is forced through lumen 206 towards lumen 204.

When the flow of electrical current from power supply 304 to actuator 246' is interrupted, the SMA comprising the actuator begins to cool, which causes the austenite crystals in its molecular structure to break apart and reform as martensite crystals. At the onset of martensite crystal formation, the shape memory effect causes actuator 246' to rapidly revert from a substantially straight rod shape to the serpentine shape of actuator 246. Further, the shape change causes piston head 244 to move downwardly. The downward movement breaks the fluid seal of lip 274 against the inner walls of lumen 206 so that fluid freely flows past lip 274.

Figure 16A:
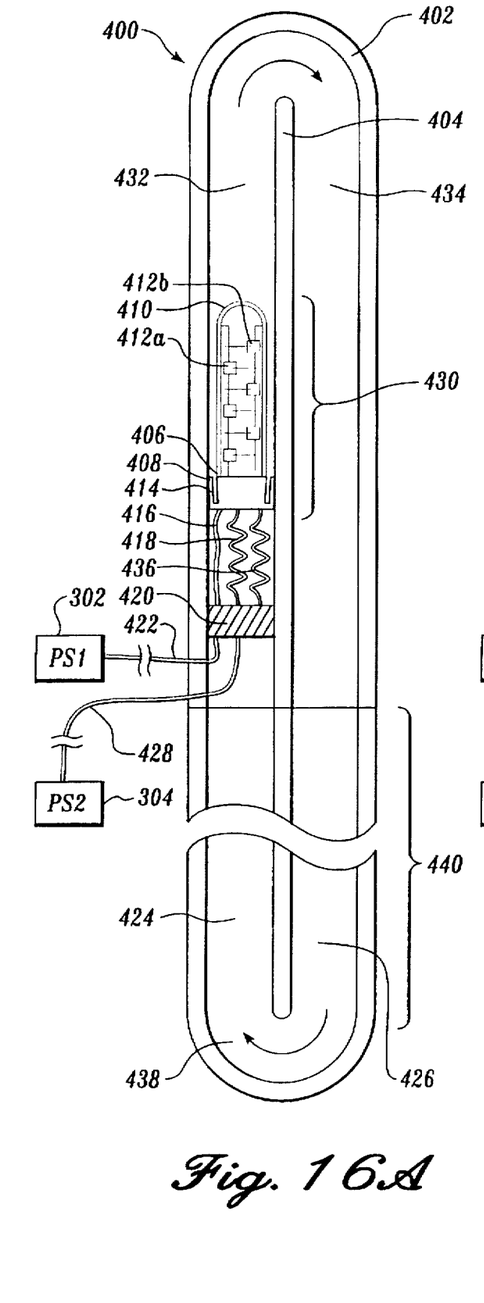
FIG. 16A is a side sectional view of a probe including an elongated sheath having two lumens and a piston coupled to an actuator, illustrating the piston and the actuator in a retracted position.
Figure 16B:
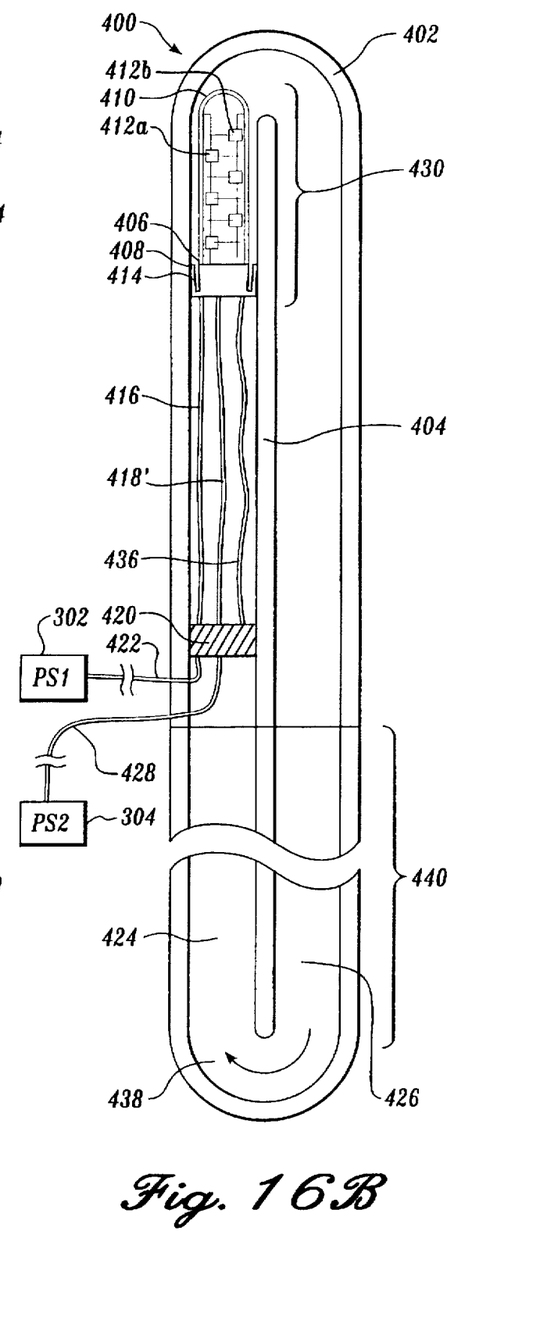
FIG. 16B is a side sectional view of the probe of FIG. 16A, displaying the piston and the actuator in an extended position.

A probe 400, comprising a seventh embodiment of the present invention, is illustrated in FIGS. 16A and 16B. Although the seventh embodiment is substantially similar to the sixth, there is an important difference between the two embodiments. In particular, the seventh embodiment includes a circuit board 410 on which are mounted light emitting devices 412a and 412b. Further, a sheath 402 comprising a transparent, biocompatible polymer material hermetically encloses the probe. Cylindrical lumens 432 and 434 are defined within the sheath and are separated by a divider 404.

In FIG. 16A, a piston assembly 430 includes a piston head 406, a base 420, a lead 436, and an actuator 418 having a serpentine shape. The electrical current from second power supply 304 is coupled through a lead 428 and lead 436 to opposite ends of actuator 418. Similarly, electrical current from first power supply 302 is carried through a lead 422 and a lead 416 to light emitting devices 412a and 412b, which are mounted on circuit board 410. In FIG. 16B, piston assembly 430 is shown with actuator 418' fully extended and configured as a substantially straight rod.

The seventh embodiment of the present invention pumps fluid through lumens 432 and 434 in substantially the same manner as discussed for the sixth embodiment, the only significant difference between the sixth and seventh embodiments being that in probe 400, the light emitting devices that administer PDT to tissue surrounding the elongated sheath are also moved with piston head 406 so that the light they emit is directed to different parts of a longitudinally extending treatment site. Thus, the seventh embodiment both cools the tissue adjacent to the treatment site by circulating fluid and also extends the area over which the PDT is administered by moving the light source within the probe to irradiate different portions of the treatment site.

Figure 17A:
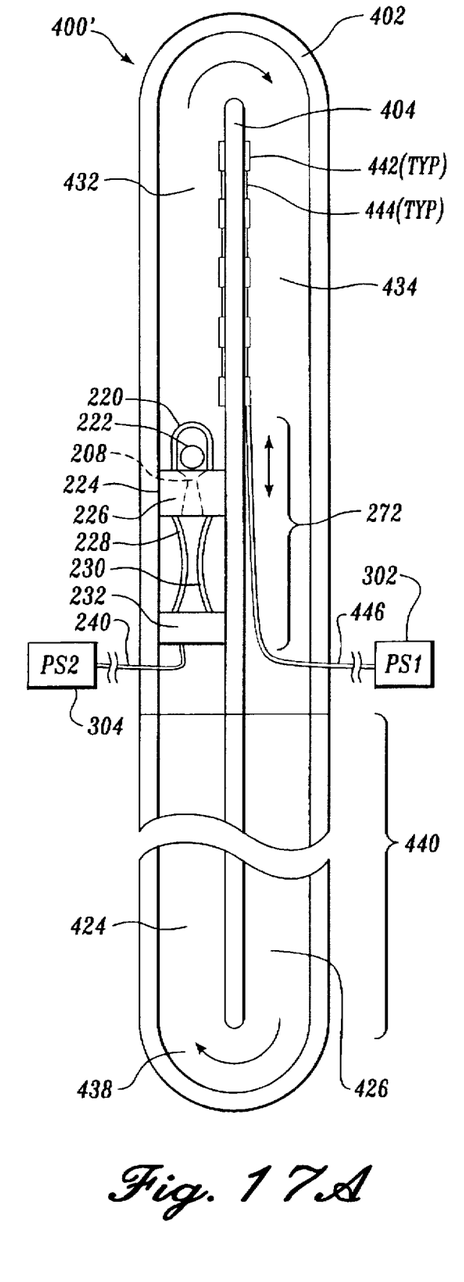
FIG. 17A is a side sectional view of a probe including an elongated sheath having two lumens separated by a divider on which are mounted a plurality of light emitting devices, and a piston assembly coupled to a pair of SMA actuators, illustrating the piston assembly in a first position in which the actuators are retracted.
Figure 17B:
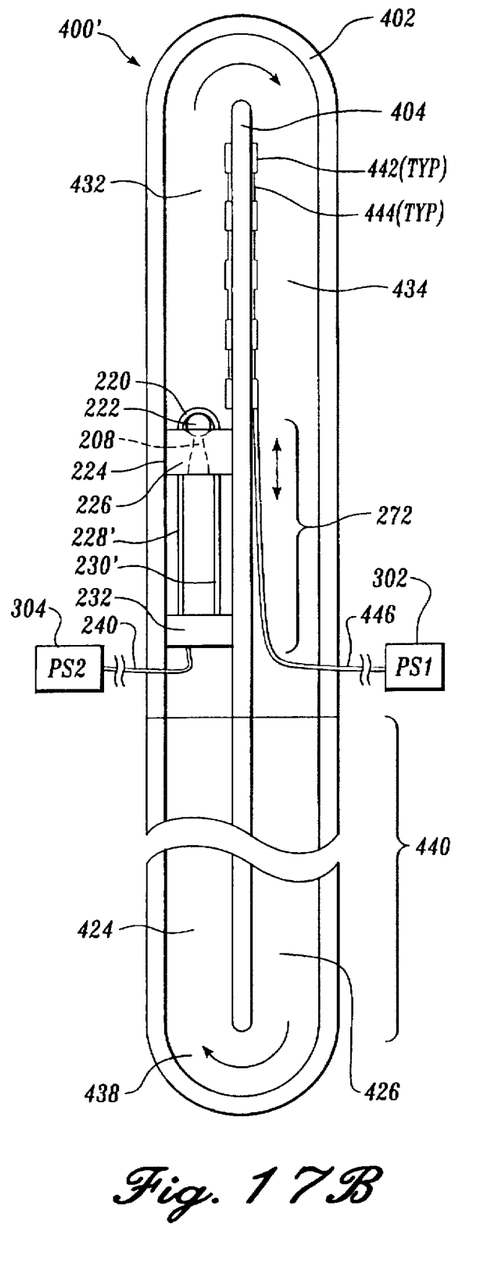
FIG. 17B is a side sectional view of the probe of FIG. 17A, illustrating the piston assembly in a second position in which the actuators are extended.
Figure 18:
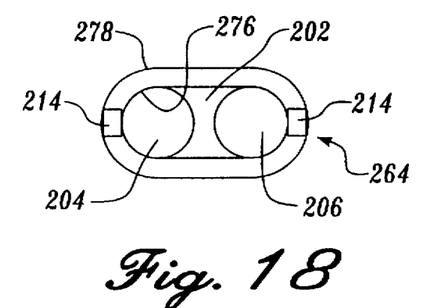
FIG. 18 is a cross-sectional view of the elongated sheath for the probe of FIG. 11A, showing the pair of cylindrical lumens separated by a divider.
Figure 19:
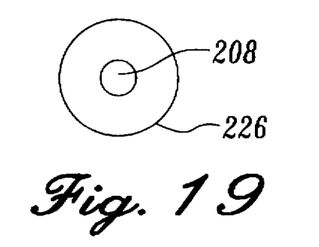
FIG. 19 is a top view of the piston head for the probe of FIG. 11A, displaying the orifice that enables fluid flow through the elongated sheath.

An eighth embodiment of the present invention is shown in FIGS. 17A and 17B. These Figures show a probe 400' having a plurality of light emitting devices 442 mounted on divider 404; the light emitting devices are coupled through a plurality of leads 444 and a lead 446 to first power supply 302, so that they are energized to emit light that is transmitted through sheath 402 to provide light therapy to surrounding tissue at the treatment site. Further, the interior of sheath 402 has a pair of lumens 432 and 434 that are separated by divider 404, except at the distal end of the sheath. The same piston assembly 272 employed in probe 200 from FIG. 11A and 11B is used in probe 400 to circulate fluid within lumens 432 and 434, so that the heat generated by light emitting devices 442 is dissipated remotely within a catheter 440 that is coupled to the probe. Probe 400' is employed in substantially the same manner as probe 200. The only significant difference between the two embodiments is the disposition of the light emitting devices that provide PDT to tissue surrounding the probes.

Although the above-described preferred embodiments that provide for circulating a cooling fluid all employ a pump that has a piston, it is also contemplated that the SMA actuator can be coupled to an elastomeric diaphragm that displaces the fluid from a pumping chamber as the diaphragm is reciprocatively displaced into and out of the pumping chamber by the SMA actuator. Diaphragm pumps driven by conventional prime movers (e.g., an electric motor) are well known to those of ordinary skill in the art and thus, are not shown in the drawings. It will be apparent that use of the SMA actuator to drive an elastomeric diaphragm represents a novel and non-obvious approach for circulating a cooling fluid through a probe, just as the use of the SMA actuator coupled to a piston, as disclosed above.

It is envisioned that the temperature of an implanted probe can be thermostatically controlled by controlling the flow of fluid through an elongated sheath having a pair of lumens. Thus, by using a thermostatic control to selectively control the application of a pulsed electrical current to the actuators of any of probes 200, 200', 400, or 400', the fluid can be pumped only when the temperature of the probe or its surrounding tissue exceeds a predetermined set point limit. Also, as an alternative to heating the actuators with an electrical current, a Peltier junction or other type of heat source/sink can be employed for changing the temperature of the actuators sufficiently that the actuators experience a memory shape change.

The SMA actuator employed in the present invention can have a single shape memory or two shape memories. In addition, there are alternative embodiments that can employ one or more SMA actuators to move a device between two positions. For example, one SMA actuator having a single shape memory can be employed to move a device in the probe in a first direction, and a second SMA actuator also having a single shape memory (but opposite in the direction in which it changes shape) can be employed to move the device in a second, opposite direction. Also, an elastomeric member or spring metal element can be elastically compressed, extended, or rotated by the SMA actuator to move the device to one position, and then be employed to move the device back to another position when the SMA actuator is deactivated. Thus, a combination of either two SMA actuators, or one SMA actuator and a spring element can be used in the present invention in place of the various SMA actuators having two shape memory states that are shown in the drawings.

It should be noted that the configuration of the SMA comprising the actuator used to move a device in any of the probes disclosed above can employ shape memory configurations having opposite states from those described above. For example, when heated above the temperature at which the SMA changes to the austenite crystal formation, the SMA may retract instead of becoming extended, or may become planar instead of twisted. The configurations achieved when the transition occurs between the two phases of the SMA are simply a matter of choice. Accordingly, the present invention is not limited to the details of the shape or state of the SMA used for the actuators in the probes disclosed above.

While the light emitting devices are preferably embedded within the sheaths of probes 200 or 200', it is also contemplated that the sheaths can be double-walled so that light sources are disposed between the walls and that the outer wall will be substantially transparent. In either case, the light emitting devices are prevented from directly contacting either a patient's tissue or the fluid circulating within the sheath. Also, the light emitting devices can comprise a variety of light sources suitable for providing light therapy, including LEDs, fiber optic filaments, incandescent bulbs, electroluminescent sources and fluorescent sources.

In the text above, a piston is recited that is positioned within the medical device and provides for the circulation of a coolant through the device. However, it is envisioned that a variety of pumping mechanisms can also be employed for circulating the coolant that are not directly disposed within the device. For example, a pumping mechanism, which is positioned external to the medical device, could be used to circulate a coolant through the device. Further, the pumping mechanism could be controlled by a remotely located thermostat, which would be used to determine the ambient temperature of the medical device within the patient's body. Also, the coolant could be circulated from a remotely located reservoir through the device. Furthermore, the claimed invention is not limited to only a first and second lumen for the circulation of a coolant through the medical device. It is also envisioned that a plurality of lumens could be employed to circulate a fluid through the device i.e., multiple intake and exhaust lumens disposed along the longitudinal axis of the medical device so as to provide site specific cooling for the device.

Although the present invention has been described in connection with several preferred forms of practicing it, those of ordinary skill in the art will understand that many more modifications can be made thereto within the scope of the claims that follow. Accordingly, it is not intended that the scope of the invention in any way be limited by the above description of the preferred embodiments, but instead be determined entirely by reference to the claims that follow.

The invention in which an exclusive right is claimed is defined by the following:

1. Apparatus that includes an enclosed probe in which a position of a device within the probe is selectively changed, comprising:
   (a) an actuator comprising a shape memory metal, said shape memory metal having a first shape associated with a first state and a second shape associated with a second state, and changing from said first state to said second state as a function of temperature;

(b) a device that is movably coupled to the actuator;

(c) an elongated sheath encapsulating the device and the actuator, said sheath having a proximal end and a distal end; and (d) means for changing the temperature of the actuator, causing it to transition from the first state to the second state, moving the device within the sheath.

2. The apparatus of claim 1, wherein the first shape of the actuator is a coiled helix and in its second shape, the actuator is substantially straighter and substantially longer than when in its first shape.

3. The apparatus of claim 1, wherein the actuator rotates through a substantial angle when transitioning between the first shape and the second shape, thereby rotating the device within the sheath.

4. The apparatus of claim 1, wherein the first shape of the actuator is serpentine and the second shape of the actuator is substantially straight, said actuator moving the device along a longitudinal axis of the probe that extends between the distal and proximal ends of the sheath as the actuator transitions between the first shape and the second shape.

5. The apparatus of claim 1, wherein the actuator comprises a plurality of shape memory metal elements.

6. The apparatus of claim 1, wherein the actuator is elongate and has two opposite ends, said actuator twisting as the actuator transitions from the first shape to the second shape, causing the device to rotate about an axis.

7. The apparatus of claim 1, wherein the device comprises a light source.

8. The apparatus of claim 7, wherein the light source comprises a plurality of light emitting devices.

9. The apparatus of claim 7, wherein the light source comprises one of a light emitting diode, a laser source, an incandescent source, a fluorescent source, and an electroluminescent source.

10. The apparatus of claim 1, wherein the means for changing the temperature comprise a resistive heating element that produces heat to change the temperature of the actuator when the resistive heating element is energized with an electrical current.

11. The apparatus of claim 1, wherein the means for changing the temperature comprise one of a thermal source that is hotter than the actuator and conveys thermal energy to the actuator to heat the actuator, and a thermal sink that is colder than the actuator and conducts thermal energy away from the actuator to cool the actuator.

12. The apparatus of claim 1, wherein the probe comprises a first lumen and a second lumen, and a pump, and wherein the probe further comprises:

(a) a heat exchanger having an inlet coupled in fluid communication with the first lumen, and an outlet coupled in fluid communication with the second lumen, said first lumen, second lumen, and heat exchanger comprising a closed fluid path, said pump being disposed in the closed fluid path;

(b) a check valve disposed in the closed fluid path, said check valve permitting fluid to flow in the closed fluid path in a first direction, but preventing fluid flow in the closed fluid path in a second direction that is generally opposite the first direction; and (c) a heat transfer fluid disposed within the closed fluid path, said heat transfer fluid conveying heat away from the probe and dissipating the heat in the heat exchanger when circulated along the closed fluid path, said pump being coupled to the actuator and driven by the actuator to cause the heat transfer fluid to circulate, as the actuator transitions between the first and the second shapes.

13. The apparatus of claim 12, wherein the pump further comprises a piston that causes the heat transfer fluid to circulate along the closed fluid path.

14. The apparatus of claim 12, wherein the device further comprises a light source that generates the heat that is conveyed away from the probe by the heat transfer fluid.

15. The apparatus of claim 14, wherein the light source is mounted on a divider disposed between the first and second lumens.

16. The apparatus of claim 13, wherein the piston is disposed within one of the first and second lumens and includes a seal around a periphery of the piston, said seal preventing the heat transfer fluid from flowing past the periphery of the piston at least when the piston is moving in the first direction.

17. The apparatus of claim 13, wherein the check valve comprises a captive ball that seals an orifice through the piston when the piston is moving in the first direction, but moves away from the orifice to permit the heat transfer fluid to flow through the orifice when the piston is moving in the second direction.

18. The apparatus of claim 16, wherein the check valve comprises the seal, said seal including an elastomeric flange around its periphery that moves radially inward toward a center of the piston and enables the heat transfer fluid to flow past the flange as the piston is displaced in the second direction, but is forced radially outward by a pressure developed in the heat transfer fluid and prevents fluid flow past the piston as the piston is displaced in the first direction.

19. The apparatus of claim 12, wherein the heat exchanger comprises a section of catheter that is coupled to the probe, said section of catheter also including a first lumen and a second lumen that are respectively coupled to the first and second lumens in the probe and are coupled together in fluid communication by a crossover path disposed at a point spaced apart from the probe.

20. The apparatus of claim 1, wherein the actuator comprises a Nitinol alloy.

21. The apparatus of claim 1, wherein the sheath comprises a material that is biocompatible and optically transparent.

22. The apparatus of claim 1, further comprising a plurality of light sources disposed within the sheath.

23. A method for changing a position of a device within a probe that is disposed within a patient's body, comprising the steps of:

(a) coupling the device to an actuator that is disposed within the probe, the device and the actuator being encapsulated by a sheath, said actuator comprising a shape memory metal that has a first shape associated with a first state and a second shape associated with a second state;

(b) heating the actuator, causing the shape memory metal to change from said first state to said second state as a function of temperature; and (c) moving the device inside the sheath with the actuator as the actuator changes between said first shape and said second shape.

24. The method of claim 23, wherein the device comprises a light source, further comprising the step of directing light emitted by the light source onto different portions of a treatment site adjacent to where the probe is disposed, by selectively heating the actuator so that it changes between the first state and the second state and when changing from the first shape to the second shape, moves the light source within the probe.

25. The method of claim 23, wherein the actuator moves the device in a direction generally aligned with a longitudinal axis of the probe when the shape memory metal changes between the first state and the second state.

26. The method of claim 23, wherein the actuator rotates the device through a substantial angle when the shape memory metal changes between the first state and the second state.

27. The method of claim 23, wherein the device comprises a piston coupled to the actuator, further comprising the step of cooling the probe with a fluid that is pumped through the probe as the actuator reciprocates the piston in response to the shape memory metal transitioning between the first and second states.

28. The method of claim 27, wherein the actuator is heated by the fluid, causing the actuator to pump the fluid with the piston as the actuator moves the piston in a first direction, and as the actuator is cooled by the fluid so that the shape memory metal transitions to the second state, the actuator drives the piston in a second direction, generally opposite to the first direction, said piston being thus alternately driven in the first and second directions by the actuator.

* * * * *